United States Patent
Palero et al.

(10) Patent No.: US 11,446,085 B2
(45) Date of Patent: Sep. 20, 2022

(54) SKIN TREATMENT METHOD AND APPARATUS

(71) Applicant: KONINKLIJKE PHILIPS N.V., Eindhoven (NL)

(72) Inventors: Jonathan Alambra Palero, Eindhoven (NL); Rieko Verhagen, Eindhoven (NL); Martin Jurna, Eindhoven (NL); Margaret Ruth Horton, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 53 days.

(21) Appl. No.: 14/429,487

(22) PCT Filed: Sep. 19, 2013

(86) PCT No.: PCT/IB2013/058661
§ 371 (c)(1),
(2) Date: Mar. 19, 2015

(87) PCT Pub. No.: WO2014/045216
PCT Pub. Date: Mar. 27, 2014

(65) Prior Publication Data
US 2015/0238258 A1   Aug. 27, 2015

Related U.S. Application Data

(60) Provisional application No. 61/703,413, filed on Sep. 20, 2012.

(51) Int. Cl.
*A61B 18/20* (2006.01)
*A61N 7/00* (2006.01)
*A61B 18/00* (2006.01)

(52) U.S. Cl.
CPC ............. *A61B 18/203* (2013.01); *A61N 7/00* (2013.01); *A61B 2018/0047* (2013.01); *A61N 2007/0034* (2013.01)

(58) Field of Classification Search
CPC ........ A61B 18/203; A61B 2018/00452; A61B 2018/00476
(Continued)

(56) References Cited

U.S. PATENT DOCUMENTS 6,174,325 B1   1/2001   Eckhouse
6,881,212 B1   4/2005   Clement
(Continued)

FOREIGN PATENT DOCUMENTS

RU   2234960 C1   8/2004
RU   2437691 C2   12/2011
(Continued)

OTHER PUBLICATIONS

Karimipour, D.J. et al., "Molecular Analysis of Aggressive Microdermabrasion in Photoaged Skin" Arch Dermatol, 2009. 145(10): p. 1114-1122.
(Continued)

*Primary Examiner* — Daniel L Cerioni

(57) ABSTRACT

A method of treating a skin tissue area, in particular non-invasively treating the skin tissue area (1), is provided. The skin tissue area has a dermis layer area (3), an epidermis layer area (5) providing a skin surface (7) and covering the dermis layer area. The method comprises: a first step of causing one or more dermal lesions (11) localized in the dermis layer area while avoiding epidermal damage, and a second step of causing, separately from causing said plurality of dermal lesions, a plurality of epidermal lesions (15) localized in the epidermis layer area. An apparatus is also provided.

19 Claims, 4 Drawing Sheets

(58) Field of Classification Search
USPC .......................................................... 606/9
See application file for complete search history.

(56) References Cited

U.S. PATENT DOCUMENTS

| | | | |
|---|---|---|---|
| 2002/0161357 A1* | 10/2002 | Anderson | A61B 18/203 606/9 |
| 2005/0049582 A1* | 3/2005 | DeBenedictis | A61B 18/20 606/9 |
| 2005/0222555 A1* | 10/2005 | Manstein | A61B 18/203 606/9 |
| 2006/0079816 A1 | 4/2006 | Barthe | |
| 2006/0241442 A1 | 10/2006 | Barthe | |
| 2007/0078290 A1 | 4/2007 | Esenaliev | |
| 2008/0243110 A1 | 10/2008 | Kang | |
| 2008/0262482 A1* | 10/2008 | Hantash | A61B 18/203 606/9 |
| 2009/0069741 A1 | 3/2009 | Altshuler | |
| 2010/0145321 A1 | 6/2010 | Altshuler | |
| 2010/0204619 A1 | 8/2010 | Rosenberg | |
| 2010/0256617 A1* | 10/2010 | Domankevitz | A61B 18/203 606/9 |
| 2010/0286673 A1* | 11/2010 | Altshuler | A61N 5/0616 606/9 |
| 2011/0092966 A1 | 4/2011 | Guo | |
| 2012/0029353 A1 | 2/2012 | Slayton | |

FOREIGN PATENT DOCUMENTS

| | | |
|---|---|---|
| WO | 2003059144 A2 | 7/2003 |
| WO | 2008001284 A2 | 1/2008 |

OTHER PUBLICATIONS

Nouri, K. and M. L. Elsaie, "What is New in Fractional Resurfacing?" US Dermatology, 2009. 4(1): p. 52-54.
Habbema et al., "Minimally Invasive Non-Thermal Laser Technology Using Laser-Induced Optical Breakdown for Skin Rejuvenation", J. Biophotonics 1-6(2011) / DOI 10.1002/JBIO.201100083.

* cited by examiner

SKIN TREATMENT METHOD AND APPARATUS

This application is the U.S. National Phase application under 35 U.S.C. § 371 of International Application No. PCT/IB2013/058661, filed on Sep. 19, 2013, which claims the benefit of U.S. Provisional Application No. 61/703,413 filed on Sep. 20, 2012. These applications are hereby incorporated by reference herein.

TECHNICAL FIELD OF THE INVENTION

The present disclosure relates to treatment of skin tissue, in particular to skin rejuvenation.

BACKGROUND OF THE INVENTION

It is known that skin rejuvenation can be induced by applying a plurality of small tissue lesions in the dermis layer of the skin tissue in a controlled manner, wherein the subsequent natural healing response of the skin tissue causes the desired rejuvenation of the skin tissue. Inflicting such lesions may be ablative or non-ablative. In ablative and non-ablative skin rejuvenation treatments, side effects have been reported including pain, erythema, edema, infections, post-inflammatory hypo-/hyper-pigmentation (PIH), blisters and scarring. Most of these side effects, specifically those related to inflammation, have been attributed to the high amount of damage to the epidermis.

Skin rejuvenation techniques sparing the epidermis have been sought after. E.g. US 2006/241442 discloses a method and a device for skin treatment using delivery of ultrasound energy into skin tissue to produce localized zones of thermal ablation, and WO 2008/001284 discloses a method and a device for skin treatment using delivery of focused optical energy into the dermis layer of the skin to cause a laser induced optical breakdown event in the dermis layer.

However, further improvements in skin rejuvenation are desired, which promote healing and further reduce pain, downtime and/or risks of complications.

SUMMARY OF THE INVENTION

A method of treating a skin tissue area, in particular non-invasively treating the skin tissue area, is herewith provided. The skin tissue area has a dermis layer area, an epidermis layer area providing a skin surface and covering the dermis layer area. The method comprises a first step of causing one or more dermal lesions localized in the dermis layer area while avoiding epidermal damage, and a second step of causing, separately from causing said one or more dermal lesions, a plurality of epidermal lesions localized in the epidermis layer area.

In the method, both dermis and epidermis lesions are caused substantially independently. The one or more dermal lesions are localized in the dermis layer area, in particular without substantially extending into other skin tissue layers and without substantially damaging the epidermis layer, and the epidermal lesions are localized in the epidermis layer area without substantially damaging the dermis layer, by virtue of which the stratum corneum and the epidermal-dermal junction can also be stimulated. This enables accurate distribution of the respective lesions and facilitates optimization of the rejuvenation and healing effects while reducing chances of infections and/or other complications.

The dermal and epidermal lesions may differ with respect to the extent of damage, e.g. ranging from retaining viability, to necrosis, and/or removal of the affected tissue such as by ablation, and/or the cause of the respective lesions such as thermally induced, mechanically induced and/or otherwise.

It has been found that the generally desired localized dermal treatments, without injury to the epidermis, tend to result in undesirably slow skin tissue regeneration and long downtime. It is considered that this slow healing is the result of a lack of efficient signalling pathways to stimulate tissue regeneration of dermal components such as collagen and elastin. In the presently provided method, epidermal lesions are caused and these promote the synthesis of epidermal growth factors by inducing a cascade of inflammatory repair and dermal remodeling responses. Thus, healing and remodeling of the dermis layer and the skin tissue area as a whole are accelerated. The presently provided combination of causing one or more dermal lesions and separate, more superficial, epidermal lesions has been found to provide an unexpectedly accelerated healing response with possibly increased collagen synthesis compared to either dermal or epidermal treatment alone.

In an embodiment, a plurality of dermal lesions may be arranged in a first pattern and the epidermal lesions may be arranged in a second, different, pattern. The first and second patterns may differ from each other with respect to size, number, lateral position and/or nature of the respective lesions, e.g. ablative or non-ablative lesions and/or mechanically, thermally or otherwise induced lesions.

In a particular embodiment, the one or more dermal lesions provide a first coverage of the skin tissue area and the plurality of epidermal lesions provide a second coverage of the skin tissue area, wherein the second coverage is at most equal to the first coverage, e.g. the first and second patterns define a first coverage and a second coverage of the skin tissue area, respectively. A suitable measure of the coverage is the percentage of the total area of the respective lesions with respect to the surface area of the treated skin tissue. It has been found that the second coverage by the epidermal lesions may be significantly smaller than the first coverage by the dermal lesions and still provide said accelerated healing, e.g. the second coverage may even be as small as a few percents of the first coverage. This facilitates reducing signs of the method, e.g. skin redness, and/or chances of complications.

In an embodiment, the first coverage of the skin tissue area is less than 40% of the skin tissue area. This coverage may also be significantly smaller, e.g. less than 25% of the skin tissue area. Preferably it is less than 5%, more preferably less than 2.5% of the skin tissue area. In this embodiment, the second coverage of the skin tissue area is less than 5% of the skin tissue area, preferably less than 1%, more preferably less than 0.5% of the skin tissue area. E.g., a first dermal coverage of about 2.5% and a second epidermal coverage of as little as 0.3% of the skin tissue area proved successful (see below) in improving or ameliorating healing. Such low effective epidermal coverages are significantly below coverages of known dermal treatments or fractional laser resurfacing treatments and they significantly reduce (the chance of) possible side effects and/or complications.

At least one of the first and second steps of causing the dermal and/or epidermal lesion(s) may comprise causing at least some of the respective dermal and/or epidermal lesions by means of focused electromagnetic energy and/or ultrasonic energy. The electromagnetic energy may preferably be in the form of laser light, in particular in the wavelength range of 300-1100 nm, and/or radiofrequency energy in a frequency range of 300 kHz 100 MHz. Ultrasonic energy may suitably have a frequency in a range of 1-500 MHz. The energy may be pulsed. For optimizing treatment of a dermis layer, or rather an epidermis layer, different values in the mentioned ranges may be chosen. Such energy sources and the effects of such energies on mammalian skin tissue are quite well known and predictable. Further, by appropriate selection of wavelengths and focusing parameters, the focus spot may be positioned accurately in the skin tissue below the surface thereof and it may have well determinable properties. Thus, the method is readily controllable and safe.

In a particular embodiment, at least one of the first and second steps of the method may comprise providing a laser beam having a laser power during a predetermined pulse time, focusing said laser beam into a focal spot in the dermis layer area and/or epidermis layer area, respectively, using a dimension of the focal spot and a power of the generated laser beam such that, in the focal spot, the laser beam has a power density which is above a characteristic threshold value for dermal or epidermal skin tissue, respectively, above which value, for the predetermined pulse time, a laser induced optical breakdown (LIOB) event occurs in the dermis layer area or epidermis layer area, respectively.

A laser induced optical breakdown (LIOB) phenomenon in the skin can be provided by providing sufficiently intense laser pulses. This LIOB is based on strong non-linear interaction of the laser light with the skin tissue, which occurs above a certain threshold value of the power density of the laser light. This causes a very localized plasma that is able to damage or even remove tissue at the location of said plasma. This is caused by secondary, primarily mechanical effects such as rapid expansion of the generated plasma. This effect is very local, because below the threshold, there is zero or very little linear and non-linear absorption, while above the threshold a plasma is generated, which even more strongly absorbs the radiation. In other words, effects such as LIOB only occur at the focal spot, while above and below the focal spot no or very much weaker effects occur. This means that for example dermal lesions may be induced by LIOB while the epidermis may easily be safeguarded against undesired effects or damage. Another safety feature against damage to the epidermis is the fact that LIOB is very efficient. A very limited amount of energy is needed to obtain the desired local effects. Likewise, LIOB may be used for causing epidermal lesions while sparing the dermal layer.

The first step of causing one or more dermal lesions may preferably occur prior to or simultaneously with the second step of causing the plurality of epidermal lesions, since lesions in the epidermis affect the tissue properties and thus can affect (predictability of) treatment of the dermis layer through the epidermis layer. E.g., transmission characteristics of electromagnetic or ultrasound energy through the epidermis may be altered, affecting (predictability of) a focal spot in the dermis layer. A time delay of up to several hours appears feasible, so that the method may be applied as two consecutive treatments, one dermal treatment and one epidermal treatment, allowing recovery of the subject and/or soothing, initial healing, etc of the subject's skin and/or moving the subject from one treatment apparatus or location to another treatment apparatus or location.

The method of treating the epidermis may comprise dermabrasion, micro-dermabrasion, and/or outer skin layer resurfacing to the skin tissue area, e.g. by applying a mechanical skin tissue perforator, a suitable light source, an ultrasound generator etc. Such apparatus facilitates inducing skin rejuvenation.

In an aspect, an apparatus for treating a skin tissue area, in particular non-invasively treating the skin tissue area, is provided. The skin tissue area has a dermis layer area and an epidermis layer area providing a skin surface and covering the dermis layer area. In particular, the apparatus is used for treating a skin tissue area according to the method disclosed herein. The apparatus comprises a first system configured to cause non-invasively one or more dermal lesions localized in the dermis layer area without causing epidermal damage, and a second system configured to cause, separately from causing said one or more dermal lesions, a plurality of epidermal lesions in the epidermis layer area.

The first and second systems preferably are configured to induce the lesions in the dermis layer area and epidermis layer area, respectively, without substantially damaging the epidermis layer and dermis layer, respectively.

Advantageously, the first and second systems are controllable so as to independently control the creation of the dermal and epidermal lesions, e.g. with respect to size, number, lateral and/or depth position of the lesions and/or extent of the skin tissue damage per lesion.

At least one of the first and second systems may comprise a source of electromagnetic and/or ultrasonic energy and a control system for directing and focusing said electromagnetic and/or ultrasonic energy in the dermis or epidermis layer area, respectively For example, at least one of the first and second systems may comprise a laser source, radiofrequency source and/or an ultrasound source.

The first and second systems may be integrated to some extent, for reasons of size, complexity, and/or energy demand, etc.

In a particular embodiment, the first and second systems comprise a common source of electromagnetic energy, e.g. a single laser source, wherein they may have at least partly different control systems for guiding and/or focusing the energy. It is noted that the first and second devices may comprise an at least partly common control system for guiding and/or focusing the energy of different energy sources, such as light at different wavelengths sent along partially overlapping beam paths. E.g., at least one of the first and second systems may comprise a laser source and an optical system comprising a first focusing portion and a second focusing portion for focusing the energy into two or more focal spots.

At least one of the first system and the second system may comprise a laser source for generating a laser beam during a predetermined pulse time, and an optical system for focusing the laser beam into a focal spot in the dermis layer area or epidermis layer area, respectively, wherein a dimension of the focal spot and a power of the generated laser beam are such that, in the focal spot, the laser beam has a power density which is above a characteristic threshold value for dermal or epidermal skin tissue, respectively, above which value, for the predetermined pulse time, a laser induced optical breakdown (LIOB) event occurs in the dermis layer area or epidermis layer area, respectively, and the optical system is arranged to position the focal spot, when the device is applied to the skin to be treated, at a treatment depth that corresponds to the dermis layer area or epidermis layer area, respectively.

In an embodiment, at least one of the first system and the second system comprises a source of ultrasonic energy, comprising a plurality of ultrasound transducers configured to focus the ultrasonic energy. The transducers may be controllable, possibly individually, with respect to period, amplitude and/or phase to control properties of the focal spot with respect to size, position, energy, duration etc.

In an embodiment, the second system comprises a (micro-)dermabrader and/or a (micro-)skin perforator, e.g. a micro-needle-studded roller, a diamond-studded scratcher, etc. to provide mechanical lesions to the epidermis.

The apparatus may be configured such that the one or more dermal lesions provide a first coverage of the skin tissue area that is less than 40% of the skin tissue area and the plurality of epidermal lesions provide a second coverage of the skin tissue area that is less than 5% of the skin tissue area.

In a preferred embodiment, the first and second systems are configured to cause the one or more dermal lesions prior to or simultaneously with the plurality of epidermal lesions.

The apparatus may comprise a controller, possibly having a memory which may be programmable, the controller being configured to operate the apparatus as a function of one or more signals from a thermometer, a colorimeter, a profilometer and/or a user interface, so as to provide one or more treatments in a controlled and safe manner. In an embodiment, a single energy source is used to deliver depth-selective independent treatments in the dermis and the epidermis. Without wishing to be bound to any specific theory, the key concept of the presently provided combined approach is considered to be based on the hypothesis that dermal injury alone does not have sufficient signalling pathways for effective regeneration of injured tissue components, while epidermal stimulation alone only results in limited regeneration of extracellular proteins because of the lack of damage or injury in the dermis. By independently controlling the amount of dermal injury and epidermal stimulation, an effective and accelerated rejuvenation treatment with minimal inflammation and downtime is achieved. It is preferred that the epidermal stimulation treatment area coverage, $T_{epidermis}$ (measured in percentage), is less than or equal to the dermal injury treatment area coverage, $T_{dermis}$, that is $T_{epidermis} \leq T_{dermis}$. The respective treatment area coverage is obtained using the relation $T_i = 100\% \times N_i \times A_i / A_{treatment}$, where $A_{treatment}$ is the total skin tissue treatment area (total of treated and untreated areas corresponding to device interface area for a plurality of elements or scanning area for scanned elements), $N_i$ is the number of lesions within the treatment, and $A_i$ the effective area of the respective lesions (i=dermis or epidermis, respectively), e.g. ¼ π $D_{focus}^2$ in the case of circular lesions.

DETAILED DESCRIPTION OF EMBODIMENTS

Figure 1:
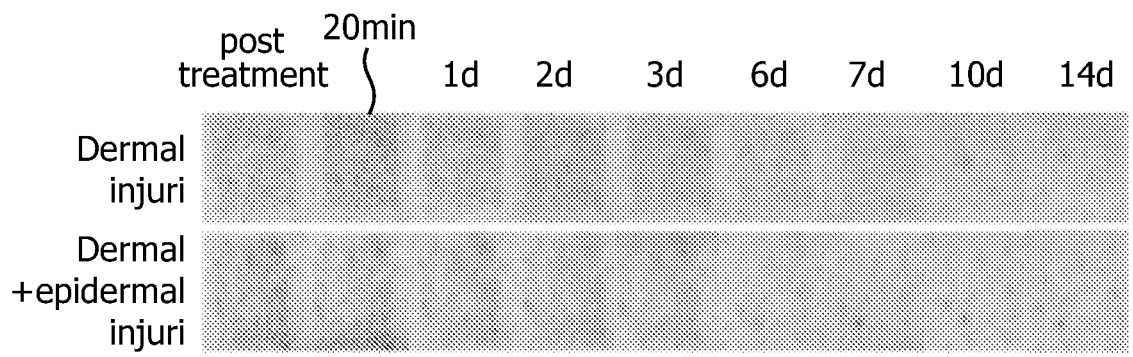
FIG. 1 shows photographs of results of a comparison test.

It is noted that in the drawings, like features may be identified with like reference signs. It is further noted that the drawings are schematic, not necessarily to scale and that details that are not required for understanding of the present invention may have been omitted. The terms "upward", "downward", "below", "above", and the like relate to the embodiments as oriented in the drawings. Further, elements that are at least substantially identical or that perform an at least substantially identical function are denoted by the same numeral.

Figure 2:
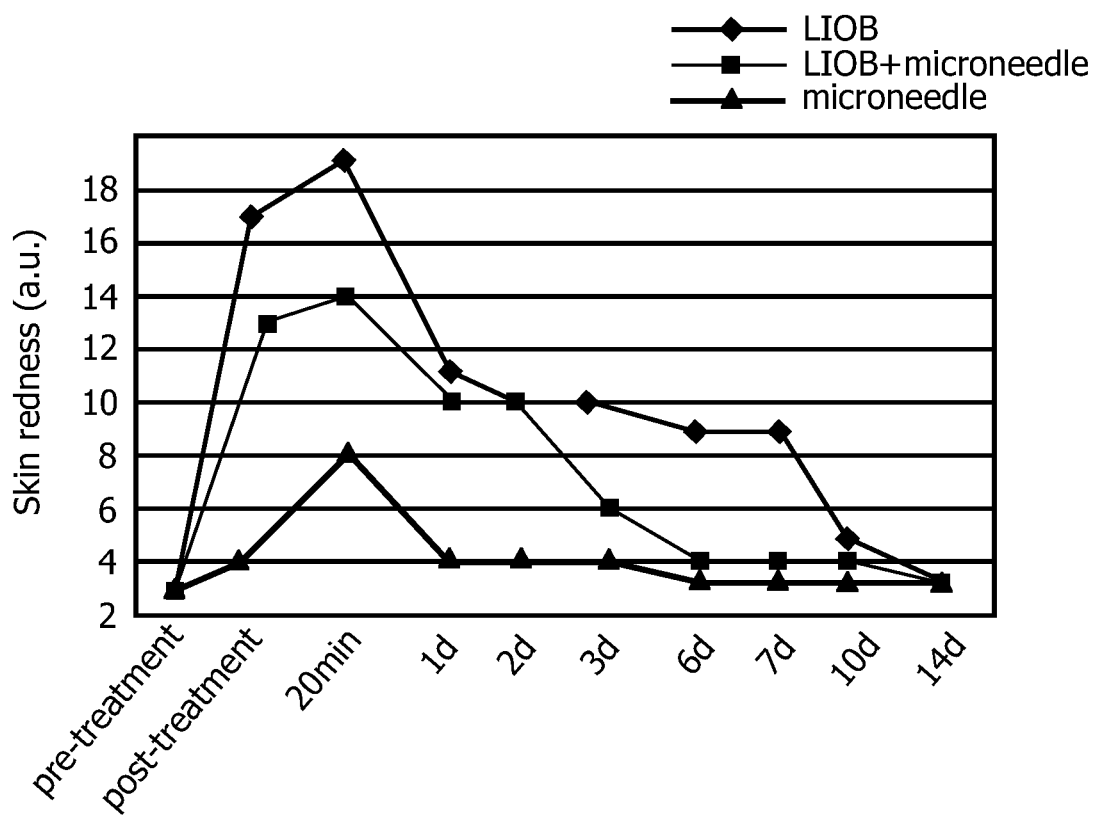
FIG. 2 is a graph illustrating test results.

FIGS. 1 and 2 show the results of a demonstration of an embodiment of a method of treating a skin tissue area in an in vivo experiment involving test volunteers, which was carried out to compare the regeneration and healing response of skin to three different treatments: 1) dermal treatment only, by non-invasively causing dermal lesions localized in the dermis layer area; 2) epidermal treatment only, by causing epidermal lesions in the epidermis layer area; and 3) both dermal treatment and epidermal treatment according to the present disclosure.

In each of the exemplary treatments, dermal injury was induced at a depth of ~180 micrometer below the skin surface, using a laser-induced optical breakdown (LIOB) skin treatment system, wherein a laser wavelength of 1064 nanometers was used with pulse energies in excess of 0.15 mJ at focus level inside the skin at a focal spot of 10 micrometers inside the skin, in accordance with Habbema et al, "Minimally invasive non-thermal laser technology using laser-induced optical breakdown for skin rejuvenation", J. Biophotonics 1-6 (2011)/DOI 10.1002/jbio.201100083. The dermal lesions provided a treatment coverage of ~2.5% of the treated skin tissue area. The epidermal treatment was provided as mechanically-induced micro-injuries into the skin through the skin surface to a depth of ~100 micrometers using a microneedle dermaroller. The epidermal treatment coverage was about ~0.3% of the skin tissue area achieved by 10 passes of the roller each providing a treatment coverage of about 0.03% of the skin tissue area.

FIG. 1 shows a series of photographs of skin treated with dermal lesions only (top row) over a fourteen-day period post treatment (photos taken immediately after treatment, after 20 minutes, and after 1, 2, 3, 6, 7, 10 and 14 days, respectively), compared with a substantially identical series of photographs of skin treated with both dermal lesions and epidermal lesions (bottom row). FIG. 2 is a graph of fourteen-day photograph and spectrophotometer (redness) test results of skin response to three types of treatment: 1) dermal injury only (diamonds—FIG. 1, top row); 2) combined dermal and epidermal injury (squares—FIG. 1, bottom row); and 3) epidermal injury (triangles no photographs shown).

The shown photographic results from subjects evidently demonstrate the faster fading of skin petechiae (red spots, FIG. 1) in the combined dermal treatment and epidermal treatment as compared to the dermal treatment alone. The epidermal treatment may be termed epidermal stimulation for its results. The experiment evidently demonstrates that introducing low treatment coverage (~0.3%, in the experiment) epidermal stimulation minimizes inflammation and accelerates the dermal healing process compared to dermal injury alone. A two- to four-fold increase in the rate of redness disappearance, which can be strongly associated with skin treatment downtime and tissue regeneration rate, is considered readily possible with the proposed combined treatment approach as compared to dermal treatment alone.

Figure 3:
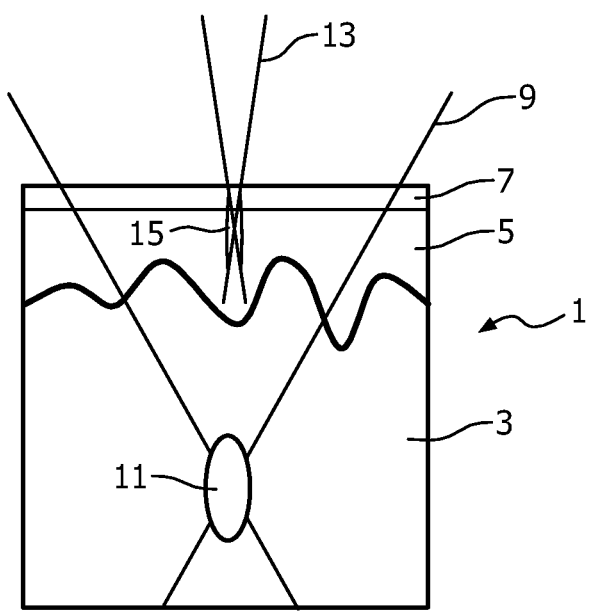
FIG. 3 illustrates an embodiment of the presently provided method.

FIG. 3 shows an alternative method of treating a skin tissue area 1 having a dermis layer area 3, an epidermis layer area 5 which covers the dermis layer area 3 and provides a skin surface 7 on top, comprising the stratum corneum. Here, a first laser beam 9 is focused to a tight focal spot within the dermis layer 3. By proper selection of, inter alia, the laser wavelength and the numerical aperture of the focusing system, the laser beam 9 is arranged such that the energy density in the focus is so high that the dermal tissue in the focal spot is damaged and a localized dermal lesion 11 is caused, whereas the energy density of the laser beam 9 in the epidermis layer 5 and the skin surface layer 7 is so low that damage to them is prevented. A second laser beam 13 is also shown, which similarly to the first laser beam 9 is focused to a tight focal spot within the epidermis layer 5 to damage it and cause a lesion 15 localized in the epidermis layer 5, without damaging the dermis layer 3 below and the surface layer 7 above. A benefit of such an embodiment over the one described above with respect to FIGS. 1 and 2 is that here also the epidermal lesions can readily be caused non-invasively without damage to the skin surface, e.g. reducing (the chances of) complications like infections.

In the embodiment of FIG. 3, the first and second laser beams 9, 13 may be generated independently and at different times, quite possibly with different laser wavelengths, from different laser sources and/or from different optical systems (neither of which is shown). The use of different laser sources and/or optical systems facilitates independent optimization of the respective treatments. E.g., one or both laser beams and foci can be chosen such that a thermal lesion is caused or such that a LIOB phenomenon is triggered in the respective skin layer area.

Figure 4:
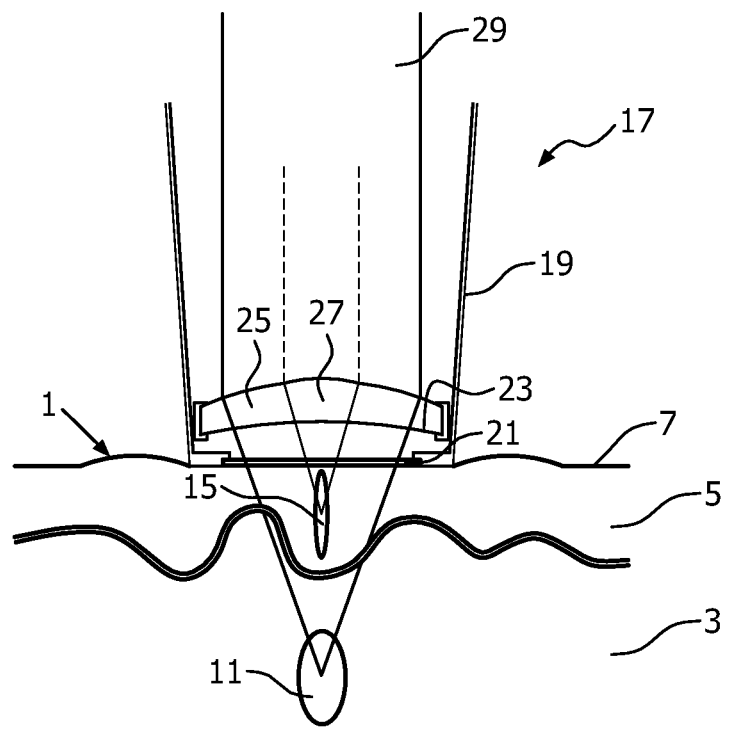
FIG. 4 illustrates an embodiment of an apparatus for performing the method of FIG. 3.

FIG. 4 shows part of a system for causing dermal and epidermal lesions substantially above each other, which is particularly suitable for simultaneously applying both dermal and epidermal treatment and/or for use with a common laser source and/or at least a partly common laser beam path. FIG. 4 again shows a skin tissue area 1 having a dermis layer area 3, an epidermis layer area 5, a skin surface 7, and dermal and epidermal lesions 11, 15, respectively, caused by independent laser foci. A portion of an optical system 17 is shown, comprising an optical beam guiding tube 19, a window 21 and a compound optical element 23, here comprising a first focusing portion in the form of a first lens portion 25 and a second focusing portion 27, here in the form of a lens portion centrally arranged in the first lens portion 25 which forms an annular lens portion 25 surrounding the central lens portion 27. Thus, the optical element 23 is configured to produce, from one incident light beam 29, two collinear but distinct and longitudinally separated focal spots so as to produce localized (epi-)dermal lesions 11, 15. The optical system 17 and window 21 may serve to protect the optical element 23 and any other optical element. The optical system 17 may provide a reference distance such that, when (the window 21 of) the system 17 is placed on the skin surface 7, the focal spots are reliably located within the desired skin tissue layers 3, 5. It is noted that instead of a window 21 any passive and/or optically effective element may be used, e.g. a lens and/or a filter.

Figure 5:
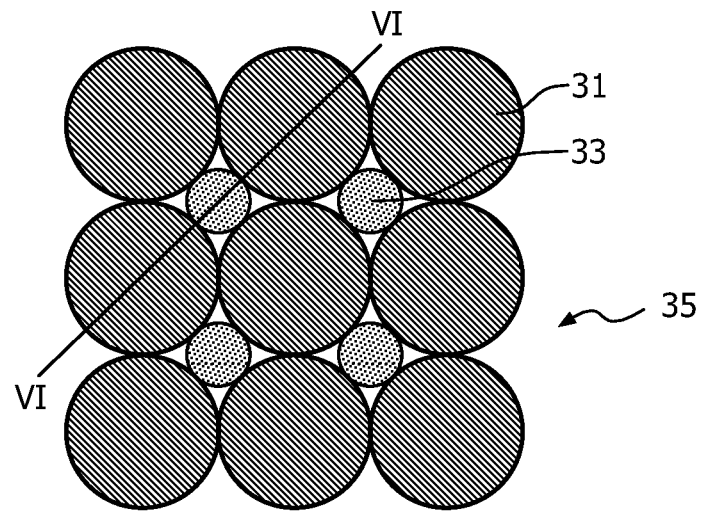
FIGS. 5 and 6 illustrate different details of an embodiment of an apparatus for performing the method of FIG. 3.
Figure 6:
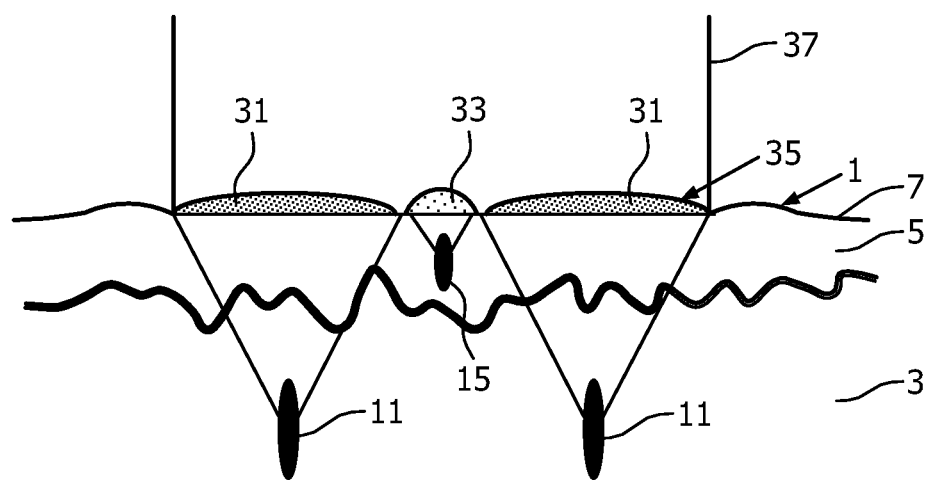

Another embodiment of a part 35 of a focusing system, suitable for the simultaneous generation of dermal and epidermal lesions, is shown in FIGS. 5 and 6. FIG. 5 shows a top view and FIG. 6 shows a cross sectional view taken on the line VI-VI of FIG. 5, like FIGS. 3 and 4. Here, too, a first focusing portion for causing dermal lesions 11 and a second focusing portion for causing epidermal lesions 15 are provided, each in the form of lenses 31 and 33, respectively. Unlike the embodiment of FIG. 4, the first and second focusing portions 31, 33, and thus the respective lesions 11, 15 are laterally offset from each other. Here, the first focusing portion 33 comprises a plurality of relatively large first lenses and the second focusing portion 31 comprises relatively small second lenses. The first lenses 31 are arranged in a square array and the second lenses 33 are arranged in the interstitial spaces in the array between the first lenses. Thus, when a sufficiently large and powerful laser beam 37 is applied, the desired dermal and epidermal lesions 11, 15 are caused simultaneously.

It is noted that in this example, the first lenses 31 are arranged in a regular array. However, any other irregular or regular arrangement e.g. hexagonal arrangement, is also conceivable. Also, the first and second focusing portions need not be arranged for causing respective lesions in comparable patterns, but the second focusing portion may be configured for causing fewer, differently located and/or further spaced apart epidermal lesions as compared to the dermal lesions, although it is conceivable that the number of epidermal lesions caused exceeds the number of dermal lesions, but is of smaller size such that the combined area of the epidermal lesions is at most equal to that of the dermal lesions.

In the embodiments of FIGS. 4-6, the energy content of the different foci may be determined by the relative density of the respective lenses and their respective surface areas, focal lengths, etc, and thus be generally reliably fixed, if no other measures like optical switches such as shutters are provided. The respective parameters of each lens may be chosen to cause thermal- or LIOB-based lesions. The focusing systems of FIGS. 4-6 may be provided with microlens-arrays, so that a plurality of lenses can be illuminated by a single laser beam and thus a plurality of dermal and epidermal lesions can be made simultaneously. It is noted that suitable focusing systems may comprise refractive and/or reflective optics, including refractive and/or reflective lenses.

By laterally scanning the laser radiation in one or two directions, parallel to the skin surface, a fractional dermal treatment and controlled epidermal stimulation can be achieved. The preferred lens parameters of a double-focus lens correspond to a configuration that produces an epidermal stimulation region whose width is appreciably smaller than the width of the produced dermal injury region, for instance an inner lens that has a larger numerical aperture (NA) than the outer lens in case of the embodiment of FIG. 4. The preferred laser wavelength range and pulse duration range to produce epidermal thermal stimulation are 0.5-2 micrometer and 0.1-40 milliseconds, respectively, while the preferred laser wavelength range and pulse duration range to produce dermal thermal injury are 0.8-11 micrometer and 0.1-40 milliseconds, respectively. The preferred laser wavelength range and pulse duration range to produce epidermal LIOB-induced stimulation are 0.7-1.5 micrometer and 50 femtoseconds −1 nanosecond, respectively, while the preferred laser wavelength range and pulse duration range to produce dermal LIOB-induced injury are 0.7-1.5 micrometer and 50 femtoseconds −1 nanosecond, respectively. In the preferred embodiments relating to light-based dermal treatments, the pulsed laser energy sources are configured to produce a maximum laser fluence of 3 $J/cm^2$ measured at the surface of the skin, taking into consideration the optical properties of the optics used, beam optical geometry (e.g. lens focal length), laser pulse duration and wavelength. In the preferred embodiments relating to light-based epidermal treatments, the pulsed laser energy sources are configured to produce a maximum laser fluence of 3 $J/cm^2$ measured at the papillary dermis, taking into consideration the optical properties of the optics used, beam optical geometry, laser pulse duration and wavelength.

Thus, the method may comprise a combination of two methods of causing thermally-induced, mechanically-induced and/or LIOB-induced dermal injury and epidermal stimulation. These two methods may be implemented using:

1) same or different energy types; 2) same or different energy source of the same energy type, more preferably the same energy type and source.

Figure 7:
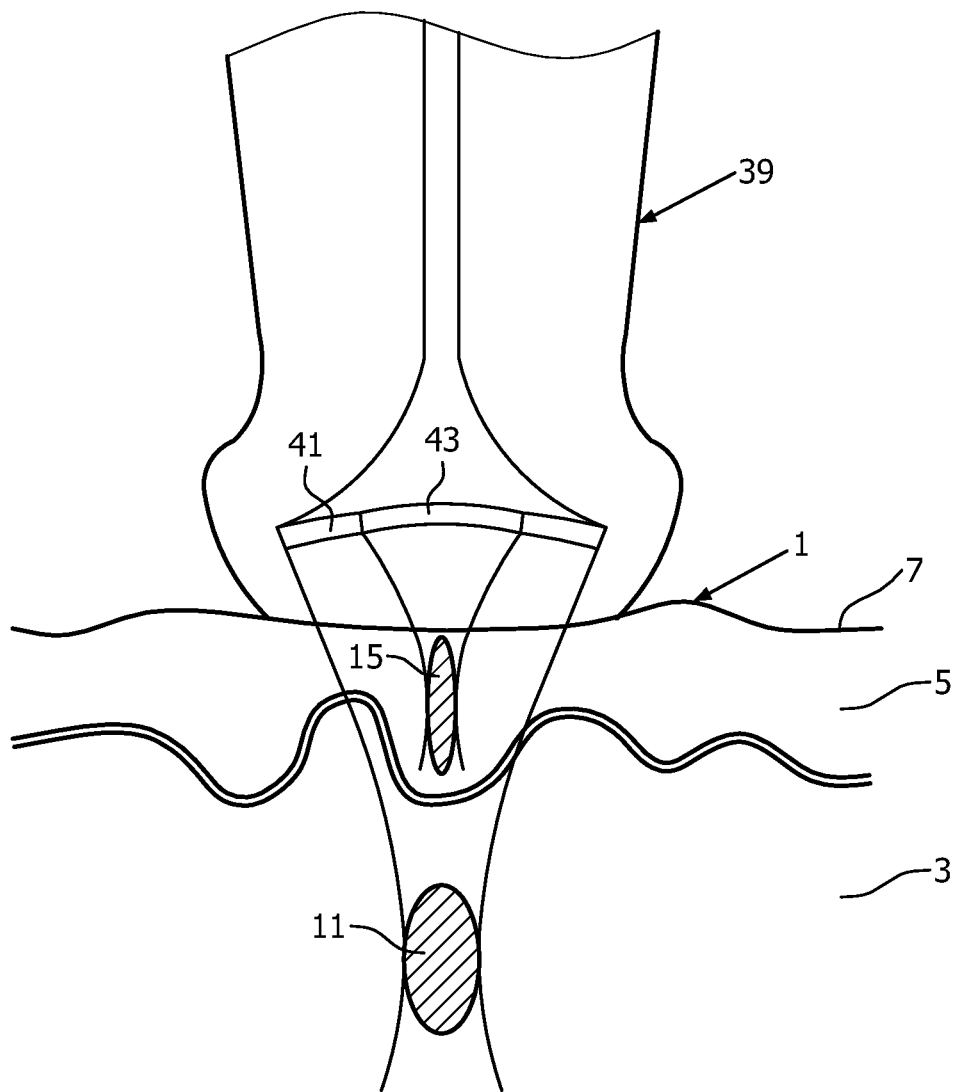
FIG. 7 illustrates another embodiment of a method and an apparatus.

Another exemplary embodiment comprises application of ultrasound energy. FIG. 7 shows part of a suitable apparatus 39 comprising two transducers 41, 43 that deliver ultrasound energy into the skin tissue area 1. The two transducers 41, 43 are configured such that they have different foci, one (41) being focused in the dermis 3 and the other (43) being focused in the epidermis 5, resulting in localized dermal thermal injury in the form of lesions 15 and localized epidermal thermal stimulation causing lesions 11. In the shown preferred embodiment, an inner single-element or multi-element (e.g. a matrix of planar elements) concave transducer 43 is focused in the epidermis 5, while an outer single-element or multi-element annular concave transducer 41 is focused in the dermis 3.

In another embodiment, one or both transducers 41, 43 can be configured as multi-element phase-array or matrix planar transducers where the focusing can be controlled by varying appropriately the relative phase of each element. This has the advantage that the treatment method can be suitably adjusted and optimized in such a way that the foci can be controlled independently of each other, e.g. to adapt to the thickness of the epidermis and depth of the dermis. Also, control of the treatment times, duration, and dosage in the epidermis and the dermis are independent of each other. The preferred ultrasonic frequency range and exposure time range to produce epidermal stimulation and dermal thermal injury are 1-500 MHz and 0.1-40 ms, respectively.

Suitable parameters for the various methods described herein, thus corresponding to apparatus properties and settings, are summarized in the following table 1:

TABLE 1 suitable parameters for performing the presently provided method.

|  | Wavelength/ frequency | Pulse duration |
|---|---|---|
| Localized epidermal treatment |  |  |
| Fractional laser | 500 nm-2 μm | 0.1-40 ms |
| (Pulsed) focused ultrasound | 1-500 MHz | 0.1-40 ms |
| Laser-induced optical breakdown | 700 nm-1.5 μm | 50 fs-1 ns |
| Localized dermal treatment |  |  |
| Fractional laser | 800 nm-11 μm | 0.1-40 ms |
| (Pulsed) focused ultrasound | 1-500 MHz | 0.1-40 ms |
| Laser-induced optical breakdown | 700 nm-1.5 μm | 50 fs-1 ns |

Although the described embodiments consist of epidermal stimulation by photo-thermally induced, ultrasound induced, thermally and/or or mechanically (including LIOB) induced injury creation, other energy sources can be used to stimulate the epidermis for improved tissue regeneration either mechanically, thermally or non-thermally (i.e. biological effects). For instance, use can be made of ultrasound cavitation, electrical radiofrequency heating, photochemical/chemical treatment, as well as other means. Furthermore, the described treatment consisting of combined dermal and epidermal skin treatments with independently controlled treatment regimes for skin rejuvenation treatment applications can be further extended to treatment of pre-existing dermal lesions, either primary, such as acne or a bruise, or secondary, such as scars. Preferred configurations include: 1) localized epidermal stimulation to promote signaling pathways for healing of the pre-existing dermal lesions, and: 2) combined localized dermal and epidermal treatments to destroy bacteria and/or viruses for infected dermal lesions by thermally-induced protein breakdown of the bacterial and viral protective membranes, and to promote signaling pathways for dermal regeneration, respectively.

It is further noted that in the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different embodiments and/or dependent claims does not indicate that a combination of these measures cannot be used to advantage. A computer program may be stored and/or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of non-invasively treating a skin tissue area, the skin tissue area including a dermis layer area in a dermis layer and an epidermis layer area in a epidermis layer, the epidermis layer area comprising a skin surface and covering the dermis layer area, the method comprising:
simultaneously producing a plurality of dermal lesions, localized in the dermis layer area, by focusing a laser beam through a plurality of first lenses into dermal focal spots at a first depth, respectively, the dermal lesions causing rejuvenation of the dermis layer area; and
simultaneously producing a plurality of epidermal lesions, separate from the dermal lesions and localized in the epidermis layer area, by focusing the laser beam through a plurality of second lenses into epidermal focal spots at a second depth less than the first depth, each epidermal lesion covering an area smaller than an area covered by each dermal lesion, such that the production of the epidermal lesion provides epidermal stimulation, which accelerates the rejuvenation of the dermis layer area caused by the dermal lesions,
wherein the first plurality of lenses are separate lenses from the second plurality of lenses and are laterally offset from each other, causing the epidermal lesions to be laterally offset from the dermal lesions, and wherein a light emitting surface of the first plurality of lenses and the second plurality of lenses are positioned along the same plane.

2. The method according to claim 1 wherein the dermal lesions collectively provide a first coverage of the skin tissue area and the epidermal lesions collectively provide a second coverage of the skin tissue area, wherein the second coverage is smaller than the first coverage.

3. The method according to claim 2, wherein the first coverage of the skin tissue area is less than 40% of the skin tissue area and wherein the second coverage of the skin tissue area is less than 5% of the skin tissue area.

4. The method according to claim 1, wherein the first plurality of lenses are arranged in an array and wherein the second plurality of lenses are arranged in the spaces in the array.

5. The method according to claim 1, wherein the laser beam comprises a fractional laser beam with a wavelength in the range of 800 nm-11 μm and a pulse duration of 0.1-40 ms.

6. The method according to claim 1, wherein producing the dermal lesions and simultaneously producing the epidermal lesions comprises:
providing the laser beam at a predetermined laser power during a predetermined pulse time;
wherein the laser beam comprises a power density in the dermal layer area or the epidermal layer area above a characteristic threshold value for the respective dermal or epidermal skin tissue at which a laser induced optical breakdown (LIOB) event is produced.

7. The method according to claim 6, wherein the laser beam for producing the laser-induced optical breakdown (LIOB) has a wavelength in the range of 700 nm-1.5 μm and a pulse duration of 50 fs-1 ns.

8. The method according to claim 1, wherein the first plurality of lenses are arranged in a pattern and the second plurality of lenses are arranged in interstitial spaces within the pattern between the first lenses.

9. The method according to claim 8, wherein the pattern of the first plurality of lenses comprises a rectangular array or a square array.

10. The method according to claim 8, wherein the pattern of the first lenses comprises a hexagonal arrangement.

11. The method according to claim 8, wherein an extent of damage by the laser beam to the dermal layer in the dermal lesions is different than an extent of damage by the laser beam to the epidermal layer in the epidermal lesions.

12. A method of non-invasively treating a skin tissue area, the skin tissue area including a dermis layer area in a dermis layer and an epidermis layer area in a epidermis layer, the epidermis layer area comprising a skin surface and covering the dermis layer area, the method comprising:
producing a plurality of dermal lesions, localized in the dermis layer area, by focusing a laser beam through a plurality of first lenses into dermal focal spots at a first depth, respectively, the dermal lesions causing rejuvenation of the dermis layer area; and
simultaneously producing a plurality of epidermal lesions, separate from the dermal lesions and localized in the epidermis layer area, by focusing the laser beam through a plurality of second lenses into epidermal focal spots at a second depth less than the first depth, each epidermal lesion covering an area smaller than an area covered by each dermal lesion, such that the production of the epidermal lesion provides epidermal stimulation, which accelerates the rejuvenation of the dermis layer area caused by the dermal lesions,
wherein the first and second lenses are laterally offset from each other, causing the epidermal lesions to be laterally offset from the dermal lesions, and
wherein the dermal lesions collectively provide a first coverage of the skin tissue area and the epidermal lesions collectively provide a second coverage of the skin tissue area, wherein the second coverage of the skin tissue area is about 12% of the first coverage of the skin tissue area.

13. The method according to claim 12, wherein producing the dermal lesions and simultaneously producing the epidermal lesions comprises:
providing the laser beam at a predetermined laser power during a predetermined pulse time;
wherein the laser beam comprises a power density in the dermal focal spots or the epidermal focal spots above a characteristic threshold value for the respective dermal or epidermal skin tissue at which a laser induced optical breakdown (LIOB) event is produced.

14. The method according to claim 12, wherein the laser beam comprises a fractional laser beam with a wavelength in the range of 800 nm-11 μm and a pulse duration of 0.1-40 ms.

15. The method according to claim 13, wherein the laser beam for producing the laser-induced optical breakdown (LIOB) comprises a wavelength in the range of 700 nm-1.5 μm and a pulse duration of 50 fs-1 ns.

16. The method according to claim 12, wherein the first lenses are arranged in a pattern and the second lenses are arranged in interstitial spaces within the pattern between the first lenses.

17. The method according to claim 16, wherein the pattern of the first lenses comprises a rectangular array or a square array.

18. The method according to claim 16, wherein the pattern of the first lenses comprises a hexagonal arrangement.

19. The method according to claim 12, wherein an extent of damage by the laser beam to the dermal layer in the dermal lesions is different than an extent of damage by the laser beam to the epidermal layer in the epidermal lesions.

* * * * *